(12) United States Patent
Jasra et al.

(10) Patent No.: US 7,544,831 B2
(45) Date of Patent: Jun. 9, 2009

(54) GREEN CATALYTIC PROCESS FOR THE SYNTHESIS OF ACETYL SALICYLIC ACID

(75) Inventors: Raksh Vir Jasra, Gujarat (IN); Beena Tyagi, Gujarat (IN); Manish Kumar Mishra, Gujarat (IN)

(73) Assignee: Council of Scientific and Industrial Research, Gujarat (IN)

( * ) Notice: Subject to any disclaimer, the term of this patent is extended or adjusted under 35 U.S.C. 154(b) by 0 days.

(21) Appl. No.: 11/859,001

(22) Filed: Sep. 21, 2007

(65) Prior Publication Data

US 2009/0082592 A1    Mar. 26, 2009

(51) Int. Cl.
*C07C 67/02* (2006.01)
*C07C 69/02* (2006.01)
*C07C 63/04* (2006.01)

(52) U.S. Cl. .................. 560/266; 560/265; 560/231; 562/493

(58) Field of Classification Search .................. None
See application file for complete search history.

(56) References Cited

OTHER PUBLICATIONS

'Catalysis' in Kirk-Othmer Encyclopedia of Chemical Technology Copyright © 2001 by John Wiley & Sons, Inc., pp. 200-253.*
Majid et al., Arkivoc (Gainesville, FL, United States) (2007), (16), 123-131.*
CAS online citation 2008:36811 [retrieved Jul. 10, 2008] from STN; Columbus OH, USA.*
Smith et al., Org. Biomol. Chem., 2003, 1, 1560-1564 (.*

\* cited by examiner

*Primary Examiner*—Karl J Puttlitz
(74) *Attorney, Agent, or Firm*—Ladas and Parry LLP

(57) ABSTRACT

The present invention provides a green catalytic process for the synthesis of acetyl salicylic acid using solid acid catalysts at atmospheric pressure. The invention involve the solid acid catalyst such as sulfated transition metal oxides namely nano-crystalline sulfated zirconia, sulfated titania; modified zeolites namely zeolite H-beta, H-Y, H-ZSM-5 and K-10 montmorillonite clay in a solvent free environment using salicylic acid and acetic anhydride with yield about 95% and high selectivity (100%). The solid acid catalysts can be recovered, regenerated and reused.

12 Claims, No Drawings

GREEN CATALYTIC PROCESS FOR THE SYNTHESIS OF ACETYL SALICYLIC ACID

FIELD OF INVENTION

The present invention relates to a green catalytic process for the synthesis of acetyl salicylic acid. Particularly the present invention relates to green catalytic process for the synthesis of acetyl salicylic acid by replacing highly corrosive and hazardous conventional liquid acid catalysts viz. conc. $H_2SO_4$ and conc. $H_3PO_4$ with easily separable solid acid catalysts. More particularly, it relates to the synthesis of acetyl salicylic acid using solid acid catalysts such as sulfated transition metal oxides namely nano-crystalline sulfated zirconia, sulfated titania; modified zeolites namely zeolite H-beta, H-Y, H-ZSM-5 and K-10 montmorillonite clay in a solvent free environment using salicylic acid and acetic anhydride with yield about 95% and high selectivity (100%).

BACKGROUND OF INVENTION

Acetyl salicylic acid is commonly known by its trade name Aspirin. Aspirin® is a registered trademark of Bayer AG in Germany and more than 80 other countries. Aspirin is an effective non-steroidal analgesic, antipyretic and anti-inflammatory drug and is one of the most widely used medicine around the world. The use of aspirin expands beyond pain relief to life saver as it reduces the risk of heart stroke by preventing the aggregation of blood platelets. The average prescribed dose of aspirin is 0.3-1 g per day, however, large single dose of 10-30 g of aspirin can results to be fatal. Today more than 10 million kilograms of aspirin is produced in US alone per year. The acetyl salicylic acid was first prepared in 1897 by Felix Hoffmann, a German chemist working for Friedrich Bayer & Co in Elberfeld and was marketed in 1899 under the registered trademark of Aspirin®. The first British patent of acetyl salicylic acid was obtained by Otto Bonhoeffer in 1900.

Acetyl salicylic acid is commercially synthesized by Kolbe-Schmidt reaction which is a multi-step process. In this process, phenol is treated with a sodium base generating sodium phenoxide, which is then reacted with carbon dioxide under high temperature (125° C.) and pressure (100 atmosphere) to yield sodium salicylate, which on acidification yields salicylic acid. Salicylic acid is then acetylated with acetic anhydride to prepare acetyl salicylic acid. Existing process of the synthesis of acetyl salicylic acid is an acid catalyzed esterification reaction by the acetylation of the salicylic acid with acetic anhydride using conventional liquid acids, namely, conc. $H_2SO_4$ or conc. $H_3PO_4$ at the temperature of 80-90° C.

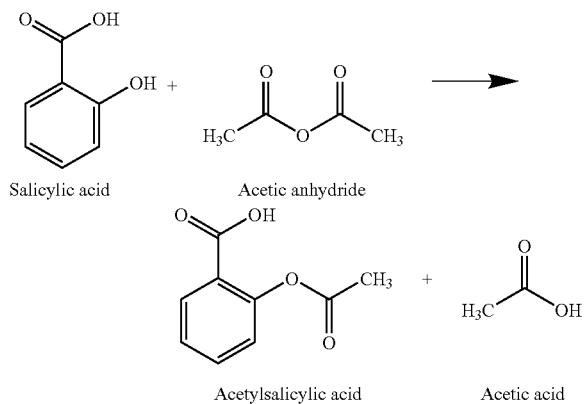

O-acetylation or esterification of salicylic acid with acetic anhydride is carried out using an acid catalyst (D. B. Brown, L. B. Friedman, *J. Chem. Educ.* 50, 214, 1973) mainly sulfuric acid (D. L. Pavia, G. M. Lampman, G. S. Kriz, *Introduction to Organic Laboratory Techniques: A Contemporary Approach*; Saunders: Philadelphia, pp 27-30, 1976) and phosphoric acid (J. A. Miller, E. F. Neuzil, *Modern Experimental Organic Chemistry*; Heath: Lexington, Mass., pp 192-197, 1982; K. L. Williamson, *Macroscale and Microscale Organic Experiments*, $2^{nd}$ Ed., Houghton Mifflin, Boston, p 379, 1994; J. Olmsted III, *J. Chem. Educ.* 75, 10, 1261, 1998) at 80-90° C. The reaction mixture is cooled in ice bath followed by addition of chilled water in the reaction mixture to hydrolyze unreacted acetic anhydride to acetic acid. The reaction mixture is kept for crystallization of acetyl salicylic acid. The crystals are separated by vacuum filtration. These processes have the drawbacks in terms of using corrosive, hazardous mineral acids, which involve post reaction work-up for the disposal of spent acid.

Reference is made to D. Y. Hung et al. in *Inter. J. Pharma* 153, 25, 1997, who have reported synthesis of acetyl salicylic acid from salicylic acid and acetic anhydride using sulfuric acid at 80° C. and salicylic acid, acetyl chloride and pyridine at 0° C. The process has a drawback in using hazardous acylating agents. Acetyl chloride causes irritation and produces hydrochloric acid during reaction. Pyridine also causes irritation and could also have adverse biological effect. Furthermore, pyridine has to be removed by dissolving the reaction mixture several times in water, which finally goes into waste water effluents.

S. Pandita et al. in *J. Chem. Educ.* 75, 770, 1998 have reported synthesis of acetyl salicylic acid from salicylic acid and acetyl chloride-pyridine in a cold water bath with 33% yield. Besides showing lower yields, the process also has the drawbacks of using acetyl chloride and pyridine.

Y. Peng et al. in *Chem. Educator* 5, 144, 2000 have reported the synthesis of acetyl salicylic acid from salicylic acid and acetic anhydride using 12-tungustophosphoric acid as a homogeneous catalyst at room temperature with 57-71% yield. The crude product was treated with sodium bicarbonate until no further bubbles were released. A gum like polymeric byproduct was formed which was removed by vacuum filtration and the filtrate was treated with 2M HCl to adjust the pH to 2. The drawback of the synthesis is the use of water-soluble 12-tungustophosphoric acid, which cannot be recovered and results in acid waste effluent. Furthermore, gummy polymeric by-product formed during the synthesis needs to be removed and the crude product is also required to be purified by the treatment with saturated sodium bicarbonate leading to increase in unit-operation to obtain the final product.

G. A. Mirafzal et al. in *J. of Chem. Edu.* 77, 3, 356, 2000 have reported the microwave assisted rapid synthesis of acetyl salicylic acid from salicylic acid and acetic anhydride using phosphoric acid as catalyst. Re-crystallization of the product in toluene resulted in a 75% yield of a pure product. This process has serious drawback as the use of corrosive and hazardous phosphoric acid is not appropriate for the use in microwave oven from the safety point of view of reaction system and the operating person, as reactor is a closed system. The separation of residual phosphoric acid from reaction mixture needs water work up and goes into waste water effluent. Toluene is also not a good solvent used for re-crystallization as it releases volatile organic vapors into the atmosphere.

A. K. Bose et al. in *Chemtech*, 18, 1997 have also reported the synthesis of acetyl salicylic acid from salicylic acid and a slightly more than molar equivalent of acetic anhydride using phosphoric acid as catalyst in domestic microwave oven. The synthesis was then carried out on 500-800 g scale using commercial microwave applicators with 80% yield. This process has serious drawback as the use of corrosive and hazardous phosphoric acid is not appropriate to use in microwave oven from the safety point of view of reaction system and operating person, as reactor is a closed system.

A. K. Bose et al. in *Fifth International Electronic Conference on Synthetic Organic Chemistry* (*ECSOC*-5) September 2001 further extended the synthesis of acetyl salicylic acid from salicylic acid and acetic anhydride using phosphoric acid as a catalyst in microwave reactor for 5 minutes by adding 1% magnesium sulfate as an additional microwave energy absorber and for excellent crystal formation of acetyl salicylic acid. The yield of acetyl salicylic acid in these experiments was in the range of 86-97%. The drawback of this process is also the use of corrosive and hazardous phosphoric acid in microwave oven and the resulting acid waste water effluent.

I. Montes et al. in *J. of Chem. Edu.* 83, 4, 628, 2006 have reported the microwave assisted synthesis of acetyl salicylic acid from salicylic acid and acetic anhydride using different acidic catalysts namely $H_2SO_4$, $H_3PO_4$, $AlCl_3$, $MgBr_2.OEt_2$ and basic catalysts namely $CaCO_3$, NaOAc, $NEt_3$ and dimethylaminopyridine. The yield of the pure acetyl salicylic acid obtained was in the range of 30-77%. However, the drawback of the process is that all the catalysts used for the synthesis are highly corrosive and need to be handled with care in closed system of microwave synthesis. Furthermore, by using an acidic catalyst, an unwanted polymeric by-product is also formed.

Therefore, the existing process for the synthesis of acetyl salicylic acid is beset with serious drawbacks. For example, the use of hazardous mineral acids is not safe from handling point of view, as these are corrosive and irritant; difficult to separate after the reaction and therefore encounters the problem of spent acid disposal. Furthermore, to recover and crystallize the crude acetyl salicylic acid product from the reaction mixture is also a time consuming tedious process and results into low yield of the product. Besides, a brown liquid impurity also appears during re-crystallization of acetyl salicylic acid from water, usually in trace amount but sometimes it is also formed in large quantity, and needs to be removed by filtering the hot aqueous solution and thus making crystallization process tedious and results into acetyl salicylic acid crystals of low purity.

Therefore, methodology to synthesize acetyl salicylic acid to overcome the above mentioned disadvantages employing an eco-friendly and safer catalyst with high yield of acetyl salicylic acid crystals of high purity is needed.

OBJECTS OF THE INVENTION

The main object of the present invention is to provide a green catalytic process for the synthesis of acetyl salicylic acid.

Yet another object of the present invention is to provide a green catalytic process for the synthesis of acetyl salicylic acid using solid acid catalyst.

Yet another object of the present invention is to synthesize acetyl salicylic acid using solid acid catalysts such as sulfated transition metal oxides particularly sulfated zirconia and sulfated titania.

Yet another object of the present invention is to synthesize acetyl salicylic acid in a solvent free environment.

Yet another object of the present invention is to synthesize acetyl salicylic acid in a single step.

Yet another object of the present invention is to synthesize acetyl salicylic acid using nano-crystalline sulfated zirconia solid acid catalyst.

Yet another object of the present invention is for the synthesis of acetyl salicylic acid using zeolite based solid acid catalysts particularly zeolite H-beta, H-Y, H-ZSM-5.

Yet another object of the present invention is to synthesize acetyl salicylic acid using acid activated clay based solid acid catalyst particularly K-10 montmorillonite clay.

Yet another object of the present invention is to synthesize acetyl salicylic acid using solid acid catalysts to separate the crude product without any acid disposal.

Yet another object of the present invention is to synthesize acetyl salicylic acid using solid acid catalyst with high yield and purity at atmospheric pressure and moderate temperature.

SUMMARY OF THE INVENTION

Accordingly, the present invention provides a green catalytic process for the synthesis of acetyl salicylic acid which comprises reacting salicylic acid with acetic anhydride in a molar ratio of 1:2 to 1:5 in a reaction vessel in the presence of activated solid acid catalyst wherein the salicylic to catalyst weight ratio in the range of 10:1 to 250:1, heating the above said reaction mixture at a temperature in the range of 90-120° C., for a period of 30-240 minutes, followed by filtration to obtain the crude acetyl salicylic acid and recrystallising the resultant crude product with ethanol-water mixture to obtain the desire pure crystal of acetyl salicylic acid and regenerating the used catalyst by washing with acetone and activating it in air at a temperature of 350-450° C. for a period of 2-4 hrs. for further use.

In an embodiment of the present invention the purity of salicylic acid used is in the range of 85-99%.

In yet another embodiment the purity of acetic anhydride used is in the range of 85-97%.

In yet another embodiment the solid acid catalyst used is selected from the group consisting of nano-crystalline sulphated zirconia, nano-crystalline sulphated titania, modified zeolites and clay catalyst.

In yet another embodiment the size of the nano-crystalline sulphated zirconia and sulphated titania used in the range of 540 nm.

In yet another embodiment the surface area of the nano-crystalline sulphated zirconia and sulphated titania used is in the range of 85-290 $m^2/g$.

In yet another embodiment the sulfur content present in nano-crystalline sulphated zirconium and sulphated titanium is the range of 0.6-3.4 wt %.

In yet another embodiment the modified zeolite catalyst used is selected from the group consisting of 4-beta, H-Y and H-ZSM-5.

In yet another embodiment the surface area of the modified zeolite catalyst used is in the range of 380-523 $m^2/g$.

In yet another embodiment the clay catalyst used is K-10 montmorillonite.

In yet another embodiment the surface area of the K-10 montmorillonite used is in the range of 220-227 $m^2/g$.

In yet another embodiment the weight ratio of acetic anhydride to solid acid catalyst used is preferably in the range of 30:1 to 40:1.

In yet another embodiment the yield of acetyl salicylic acid obtained is in the range of 93-97%.

DETAILED DESCRIPTION OF THE INVENTION

In the present invention, we report an eco-friendly solvent free green synthesis of acetyl salicylic acid by O-acetylation of salicylic acid with acetic anhydride using solid acid catalysts such as sulfated metal oxide namely nano-crystalline sulfated-zirconia and sulfated-titania; modified zeolites namely H-beta, H-Y, H-ZSM-5; and K-10 montmorillonite clay to replace the conventional homogenous liquid acid catalysts viz sulfuric acid and phosphoric acid.

Nano-crystalline sulfated-zirconia is an efficient solid acid catalyst having sulfates as chelating bidentate species on the surface responsible for catalytic conversion at atmospheric pressure. Nano-crystalline size of the catalyst provides large fraction of active species on the surface thus enhancing the catalytic activity of the catalyst. The catalyst can be prepared by the hydrolysis of zirconium alkoxide or zirconium salts using one-step (OSG) or two-step sol-gel (TSG) technique and conventional precipitation (PPT) method at ambient temperature and atmospheric pressure. The sulfation of zirconia gel with varied concentrations of sulfuric acid can be carried out simultaneously in one-step sol-gel technique and in successive steps of two-step sol-gel technique and conventional precipitation method at ambient temperature. The zirconia gel thus prepared can be thermally dried or supercritically dried (SCD) using the critical conditions of temperature and pressure of the solvent used.

The sulfated titania catalyst was prepared using one-step sol-gel technique by the hydrolysis of titanium alkoxide with water and sulfation with concentrated sulfuric acid. The resulting gel was dried and calcined.

Zeolite H-beta, H-Y and H-ZSM-5 were prepared by treating Na-forms of the zeolites with aqueous ammonium chloride or acetate salt solution followed by filtration and washing with distilled water till the filtrate was free from chloride or acetate anions. The sample obtained was dried followed by calcination under air.

Structural characterization of all above prepared catalysts was done by FT-IR Spectroscopy and X-ray powder diffraction techniques. The crystallite size was determined from XRD data. BET surface area was measured by $N_2$ adsorption desorption isotherm study at 77.4 K. The bulk sulfur content in the sulfated-zirconia and titania samples was measured by elemental analysis. Activation of all these prepared catalysts was done at 110-450° C. for 2-10 h under static air prior to the catalytic studies.

The characteristics of nano-crystalline sulfated-zirconia prepared with varied parameters along with other solid acid catalysts are summarized in Table 1.

The synthesis of acetyl salicylic acid was carried out using nano-crystalline sulfated-zirconia and other solid acid catalysts such as sulfated-titania, zeolites and clay in liquid phase in a 20 ml reaction vessel equipped with magnetic stirrer at one atmosphere. The optimization of reaction parameters for the synthesis of the acetyl salicylic acid was carried out with nano-crystalline sulfated-zirconia catalyst. In a typical procedure, the salicylic acid and acetic anhydride were heated in a 20 ml capacity reaction tube equipped with magnetic stirrer at the temperature ranging from 90 to 120° C. for 30 to 240 minutes. The synthesis of the acetyl salicylic acid was carried out with varied molar ratio of salicylic acid to acetic anhydride such as 1:2, 1:3, 1:4 and 1:5. The synthesis of the acetyl salicylic acid was carried out with varied salicylic acid to sulfated-zirconia catalyst weight ratio ranging from 10:1 to 250:1 under similar reaction condition and at atmospheric pressure.

TABLE 1

Synthetic technique and characterization of various solid acid catalysts used for the synthesis of acetyl salicylic acid.

| Catalyst | Method | Crystalline phase | Crystallite size (nm) | Surface area (m²/g) | Sulfur (wt. %) |
|---|---|---|---|---|---|
| SZ-1 | OSG | Tetragonal | 11 | 97 | 1.9 |
| SZ-2 | OSG with double sulfation | Tetragonal + Monoclinic | 12 | 110 | 2.3 |
| SZ-3 | OSG with SCD | Tetragonal | 5 | 115 | 2.4 |
| SZ-4 | TSG | Tetragonal | 12-15 | 85-101 | 0.6-2.8 |
| SZ-5 | PPT | Tetragonal | 14-31 | 130-290 | 1.9-3.4 |
| ST | OSG | Anatase | 33 | 89 | 1.3 |
| H-beta | — | — | — | 523 | — |
| H-Y | — | — | — | 700 | — |
| H-ZSM-5 | — | — | — | 380 | — |
| K-10 | — | — | — | 220-270 | — |

The synthesis of acetyl salicylic acid was carried out from 1 to 10 g scale of salicylic acid under the similar reaction conditions resulting similar yield of acetyl salicylic with no side products.

Separation of acetyl salicylic acid from the reaction mixture was done by adding chilled water to hydrolyze unreacted acetic anhydride to acetic acid and to crystallize acetyl salicylic acid crystals from the reaction mixture at atmospheric temperature and pressure followed by filtration and re-crystallization using ethanol-water system. The product obtained was of high purity as confirmed by melting point (133-135° C.), FT-IR, and NMR Spectroscopy.

The recovered nano-crystalline sulfated-zirconia catalyst, after filtration from reaction mixture, was thermally regenerated at 450° C. for 2-4 h in air. The regenerated catalyst was used for further reaction cycles up to five cycles without loss of activity and resulting similar yield as fresh catalyst and the product obtained was of high purity as before, as confirmed by melting point, FT-IR, and NMR Spectroscopy.

The yield of the acetyl salicylic acid was calculated as:

$$\text{Yield \% of Acetyl salicylic acid} = 100 \times \frac{\text{Grams of acetyl salicylic acid obtained}}{\text{Grams of acetyl salicylic acid obtained theoritically}}$$

Sulfated zirconia and titania possess surface acidity due to binding of sulfate groups to $Zr^{4+}$ and $Ti^{4+}$ respectively. Zeolites and acid treated clay are well known solid acid catalyst for their surface acidity due to proton interaction with the substrate. The esterification of salicylic acid with acetic anhydride in presence of acid catalyst to form acetyl salicylic acid is a Brönsted acid catalyzed reaction. The mechanistic path of the reaction involves the generation of acyl carbonium ion electrophile from acetic anhydride in presence of an acid catalyst, which attacks on phenolic oxygen of salicylic acid to form acetyl salicylic acid.

The acetyl salicylic acid with high selectivity and yield in accordance with the invention can be synthesized in a solvent free environment using solid acid catalysts, which are easily separable. Salicylic acid is reacted with acetic anhydride in presence of solid acid catalyst under a wide range of variables as described in the text. The acetyl salicylic acid so prepared is re-crystallized to obtain pure crystals and the catalyst is regenerated for further reuse. The hitherto known process does not divulge nor teach how solid acid catalyst can be used for the synthesis of acetyl salicylic acid at atmospheric pressure. It is reported for the first time in the present invention how the catalytic conversion of salicylic acid to acetyl salicylic acid can be achieved in presence of solid acid catalyst in solvent free environment. The inventive steps adopted in the present invention are (i) the catalytic conversion take place in solvent free environment. This dispenses the need of the use of any solvent; (ii) solid acid catalysts can be easily recovered and reused. It alleviates the problem of separating homogeneous catalyst from the reaction product; (iii) the catalytic conversion is achieved in benign condition. The solid acid catalyst obviates the need of the use of corrosive and hazardous liquid acid catalyst; (iv) the process does not involve any post reaction workup for the disposal of corrosive and hazardous spent acid.

The following examples are given by way of illustration and therefore should not be constructed to limit the scope of the present invention.

EXAMPLE 1

0.0072 moles of salicylic acid and 0.029 moles acetic anhydride (molar ratio=1:4) were taken in a 20 ml reaction vessel of reaction station. Nano-crystalline sulfated zirconia catalyst (SZ-1), activated at 450° C. in static air with salicylic acid to catalyst weight ratio 10:1, was added and the mixture was heated at 90° C. for 30 minutes. The reaction mixture was filtered to separate the catalyst. The acetyl salicylic acid was crystallized from the reaction mixture. The crude yield of acetyl salicylic acid obtained was 75%. It was further re-crystallized with ethanol-water to obtain pure crystals of acetyl salicylic acid and was characterized by melting point, FT-IR, and NMR spectroscopy.

EXAMPLE 2

0.0072 moles of salicylic acid and 0.029 moles acetic anhydride (molar ratio=1:4) were taken in a 20 ml reaction vessel of reaction station. Nano-crystalline sulfated zirconia catalyst (SZ-1), activated at 450° C. in static air with salicylic acid to catalyst weight ratio 10:1, was added and the mixture was heated at 90° C. for 240 minutes. The reaction mixture was filtered to separate the catalyst. The acetyl salicylic acid was crystallized from the reaction mixture. The crude yield of acetyl salicylic acid was 73%. It was further re-crystallized with ethanol-water to obtain pure crystals of acetyl salicylic acid.

EXAMPLE 3

0.0072 moles of salicylic acid and 0.029 moles acetic anhydride (molar ratio=1:4) were taken in a 20 ml reaction vessel of reaction station. Nano-crystalline sulfated zirconia catalyst (SZ-1), activated at 450° C. in static air with salicylic acid to catalyst weight ratio 10:1, was added and the mixture was heated at 100° C. for 30 minutes. The reaction mixture was filtered to separate the catalyst. The acetyl salicylic acid was crystallized from the reaction mixture. The crude yield of acetyl salicylic acid was 73%. It was further re-crystallized with ethanol-water to obtain pure crystals of acetyl salicylic acid.

EXAMPLE 4

0.0072 moles of salicylic acid and 0.029 moles acetic anhydride (molar ratio=1:4) were taken in a 20 ml reaction vessel of reaction station. Nano-crystalline sulfated zirconia catalyst (SZ-1), activated at 450° C. in static air with salicylic acid to catalyst weight ratio 10:1, was added and the mixture was heated at 100° C. for 240 minutes. The reaction mixture was filtered to separate the catalyst. The acetyl salicylic acid was crystallized from the reaction mixture. The crude yield of acetyl salicylic acid was 74%. It was further re-crystallized with ethanol-water to obtain pure crystals of acetyl salicylic acid.

EXAMPLE 5

0.0072 moles of salicylic acid and 0.029 moles acetic anhydride (molar ratio=1:4) were taken in a 20 ml reaction vessel of reaction station. Nano-crystalline sulfated zirconia catalyst (SZ-1), activated at 450° C. in static air with salicylic acid to catalyst weight ratio 10:1, was added and the mixture was heated at 120° C. for 15 minutes. The reaction mixture was filtered to separate the catalyst. The acetyl salicylic acid was crystallized from the reaction mixture. The crude yield of acetyl salicylic acid was 85%. It was further re-crystallized with ethanol-water to obtain pure crystals of acetyl salicylic acid.

EXAMPLE 6

0.0072 moles of salicylic acid and 0.029 moles acetic anhydride (molar ratio=1:4) were taken in a 20 ml reaction vessel of reaction station. Nano-crystalline sulfated zirconia catalyst (SZ-1), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 92-95%. It was further re-crystallized with ethanol-water to obtain pure crystals of acetyl salicylic acid.

EXAMPLE 7

0.0072 moles of salicylic acid and 0.0145 moles acetic anhydride (molar ratio of 1:2) were taken in a 20 ml reaction tube of reaction station. Nano-crystalline sulfated zirconia catalyst (SZ-1), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 68%.

EXAMPLE 8

0.0072 moles of salicylic acid and 0.0216 moles acetic anhydride (molar ratio of 1:3) were taken in a 20 ml reaction tube of reaction station. Nano-crystalline sulfated zirconia catalyst (SZ-1), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 75%.

EXAMPLE 9

0.0072 moles of salicylic acid and 0.0360 moles acetic anhydride (molar ratio of 1:5) were taken in a 20 ml reaction tube of reaction station. Nano-crystalline sulfated zirconia catalyst (SZ-1), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 88%.

EXAMPLE 10

0.0072 moles of salicylic acid and 0.029 moles acetic anhydride (molar ratio of 1:4) were taken in a 20 ml reaction tube of reaction station equipped with magnetic stirrer. Nano-crystalline sulfated zirconia catalyst (SZ-1), activated at 450° C. in static air with salicylic acid to catalyst weight ratio 40:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 90%.

EXAMPLE 11

0.0072 moles of salicylic acid and 0.029 moles acetic anhydride (molar ratio of 1:4) were taken in a 20 ml reaction tube of reaction station. Nano-crystalline sulfated zirconia catalyst (SZ-1), activated at 450° C. in static air with salicylic acid to catalyst weight ratio 120:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 90%.

EXAMPLE 12

0.0072 moles of salicylic acid and 0.029 moles acetic anhydride (molar ratio of 1:4) were taken in a 20 ml reaction tube of reaction station. Nano-crystalline sulfated zirconia catalyst (SZ-1), activated at 450° C. in static air with salicylic acid to catalyst weight ratio 250:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 92%.

EXAMPLE 13

The preparation of acetylsalicylic acid was carried out at large scale taking 10 g salicylic acid (molar ratio of 1:4) in a 250 ml round bottom flask of reaction station. Nano-crystalline sulfated zirconia catalyst (SZ-1), activated at 450° C. in static air with salicylic acid to catalyst weight ratio 100:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 95%.

EXAMPLE 14

The recovered SZ-1 catalyst, after filtration from the reaction in example 6, was thermally regenerated at 450° C. for 2 h in static air. The reaction on the regenerated catalyst was carried out under similar reaction conditions i.e. by taking 0.0072 moles of salicylic acid and 0.029 moles acetic anhydride (molar ratio of 1:4) in a 20 ml reaction tube of reaction station equipped with magnetic stirrer. Regenerated SZ-1 catalyst was added in the reaction mixture with salicylic acid to catalyst weight ratio 10:1 and the mixture was heated at 120° C. for 30 minutes. The reaction mixture was filtered to separate the catalyst. The acetyl salicylic acid was crystallized from the reaction mixture. The catalyst was recovered and used after regeneration for further five reaction cycles. The crude yield of acetyl salicylic acid was in range of 90-95%.

EXAMPLE 15

0.0072 moles of salicylic acid and 0.029 moles acetic anhydride (molar ratio of 1:4) were taken in a 20 ml reaction tube of reaction station. Nano-crystalline sulfated zirconia catalyst (SZ-2), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 93%.

EXAMPLE 16

0.0072 moles of salicylic acid and 0.029 moles acetic anhydride (molar ratio of 1:4) were taken in a 20 ml reaction tube of reaction station. Nano-crystalline sulfated zirconia catalyst (SZ-3), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 91%.

EXAMPLE 17

0.0072 moles of salicylic acid and 0.029 moles acetic anhydride (molar ratio of 1:4) were taken in a 20 ml reaction tube of reaction station. Nano-crystalline sulfated zirconia catalyst (SZ-4), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 91-92%.

EXAMPLE 18

0.0072 moles of salicylic acid and 0.029 moles acetic anhydride (molar ratio of 1:4) were taken in a 20 ml reaction tube of reaction station. Nano-crystalline sulfated zirconia catalyst (SZ-5), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 89-92%.

EXAMPLE 19

0.0072 moles of salicylic acid and 0.029 moles acetic anhydride (molar ratio of 1:4) were taken in a 20 ml reaction tube of reaction station. Nano-crystalline sulfated titania catalyst (ST), activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 85%.

EXAMPLE 20

0.0072 moles of salicylic acid and 0.029 moles acetic anhydride (molar ratio of 1:4) were taken in a 20 ml reaction tube of reaction station. Zeolite H-beta catalyst, activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 85%.

EXAMPLE 21

0.0072 moles of salicylic acid and 0.029 moles acetic anhydride (molar ratio of 1:4) were taken in a 20 ml reaction tube of reaction station. Zeolite H—Y catalyst, activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 78%.

EXAMPLE 22

0.0072 moles of salicylic acid and 0.029 moles acetic anhydride (molar ratio of 1:4) were taken in a 20 ml reaction tube of reaction station. Zeolite ZSM-5 catalyst, activated at 450° C. in static air with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 70%.

EXAMPLE 23

0.0072 moles of salicylic acid and 0.029 moles acetic anhydride (molar ratio of 1:4) were taken in a 20 ml reaction tube of reaction station. K-10 Montmorillonite clay catalyst, activated at 110° C. in static air for 10 h with salicylic acid to catalyst weight ratio 10:1, was added and the mixture was heated at 120° C. for 30 minutes. The reaction mixture was filtered to separate the catalyst. The acetyl salicylic acid was crystallized from the reaction mixture. The crude yield of acetyl salicylic acid was 65%.

ADVANTAGES

1. The present invention provides a process for the synthesis of acetyl salicylic acid in a solvent free environment.
2. The present invention provides a single step process for the synthesis of acetyl salicylic acid.
3. The present invention provides a process for the synthesis of acetyl salicylic acid using solid acid catalyst without any acid disposal.
4. The present invention provides a process for the synthesis of acetyl salicylic acid using solid acid catalyst with high yield and purity at atmospheric pressure and moderate temperature.

The invention claimed is:

1. A green catalytic process for the synthesis of acetyl salicylic acid which comprises reacting salicylic acid with acetic anhydride in a molar ratio of 1:2 to 1:5 in the presence of solid acid catalyst wherein the solid acid catalyst used is selected from the group consisting of nano-crystalline sulphated zirconia, nano-crystalline sulphated titania, zeolite H-beta, H-Y, H-ZSM-5 and K-10 montmorillonite clay catalyst having the surface area in the range of 85-523 m2/g, wherein the salicylic acid to catalyst weight ratio in the range of 10:1 to 250:1, heating the above said reaction mixture at a temperature in the range of 90 to 120° C., for a period of 30 to 240 minutes, followed by filtration to obtain the crude acetyl salicylic and recrystallizing the resultant crude product with ethanol-water mixture to obtain pure crystals of acetyl salicylic acid and regenerating the used catalyst by washing with acetone and activating it in air at a temperature of 350 to 450° C. for a period of 2-4 hrs for further use.

2. The process according to claim 1, wherein the purity of salicylic acid used is in the range of 85-99%.

3. The process according to claim 1, wherein the purity of acetic anhydride used is in the range of 85-97%.

4. The process according to claim 1, wherein the molar ratio of salicylic acid to acetic anhydride is in the range of 1:2 to 1:5.

5. The process according to claim 1, wherein the weight ratio of salicylic acid to nano-crystalline sulfated zirconia catalyst is in the range of 10:1 to 250:1.

6. The process according to claim 1, wherein the size of the nano-crystalline sulphated zirconia used is in the range of 5-40 nm and the sulfur content present is in the range of 0.6-3.4 wt %.

7. The process according to claim 1, wherein the weight ratio of salicylic acid to sulfated titania, modified zeolite or clay catalyst is 10:1.

8. The process according to claim 1, wherein the weight ratio of acetic anhydride to nano-crystalline sulfated zirconia catalyst is in the range of 15:1 to 750:1.

9. The process according to claim 1, wherein the weight ratio of acetic anhydride to sulfated titania, modified zeolite or clay catalyst is 30:1.

10. The process according to claim 1, wherein the temperature of the reaction medium is in the range of 90 to 120° C.

11. The process according to claim 1, wherein the time of the reaction is in the range of 30 to 240 minutes.

12. The process according to claim 1, wherein the yield of acetyl acetic acid obtained is in the range of 93-97%.

* * * * *